United States Patent
Stack et al.

(10) Patent No.: US 10,987,456 B2
(45) Date of Patent: Apr. 27, 2021

(54) DEVICES FOR USE IN EXTRACTING PERCUTANEOUS VENTRICULAR ASSIST DEVICES

(71) Applicant: Synecor LLC, Chapel Hill, NC (US)

(72) Inventors: Richard S Stack, Chapel Hill, NC (US); William L Athas, Chapel Hill, NC (US); Kevin Johnson, Durham, NC (US); Salvatore Castro, Raleigh, NC (US)

(73) Assignee: Synecor LLC, Durham, NC (US)

( * ) Notice: Subject to any disclaimer, the term of this patent is extended or adjusted under 35 U.S.C. 154(b) by 0 days.

(21) Appl. No.: 16/579,779

(22) Filed: Sep. 23, 2019

(65) Prior Publication Data

US 2021/0085851 A1    Mar. 25, 2021

(51) Int. Cl.
*A61M 1/00*    (2006.01)
*A61M 1/12*    (2006.01)

(52) U.S. Cl.
CPC ......... *A61M 1/125* (2014.02); *A61M 2209/04* (2013.01); *A61M 2210/127* (2013.01)

(58) Field of Classification Search
CPC .............. A61M 1/125; A61M 2209/04; A61M 2210/127; A61B 17/320016; A61B 17/32002; A61B 2017/320032
USPC .......................................................... 600/16
See application file for complete search history.

(56) References Cited

U.S. PATENT DOCUMENTS

| | | | | |
|---|---|---|---|---|
| 5,584,803 A * | 12/1996 | Stevens | ................. | A61M 25/10 604/6.16 |
| 5,928,132 A * | 7/1999 | Leschinsky | ......... | A61M 1/1037 600/16 |
| 6,228,018 B1 * | 5/2001 | Downey | ............. | A61M 1/1075 600/18 |
| 6,409,674 B1 * | 6/2002 | Brockway | ............ | A61B 5/0028 600/486 |
| 7,022,100 B1 * | 4/2006 | Aboul-Hosn | ......... | A61M 1/125 604/6.11 |
| 8,066,628 B1 * | 11/2011 | Jeevanandam | ..... | A61M 1/1072 600/17 |
| 8,323,174 B2 * | 12/2012 | Jeevanandam | ..... | A61M 1/1072 600/17 |
| 8,550,973 B2 * | 10/2013 | Magovern | ............. | A61M 1/101 600/16 |
| 8,992,408 B2 * | 3/2015 | Magovern | ........... | A61M 1/1008 600/16 |
| 9,770,256 B2 * | 9/2017 | Cohen | ............. | A61B 17/32053 |

(Continued)

*Primary Examiner* — Carl H Layno
*Assistant Examiner* — Michael J Lau

(57) ABSTRACT

A system and method for extracting a pVAD device that is implanted with a distal portion in an aorta of the heart and a drive line extending across an inter-atrial septum and out of the body via a superior vessel of the venous vasculature, include a first device that is introduced into a femoral artery and through the descending aorta used to engage a distal part of the pVAD device in the aorta of a patient using an instrument. A second, cutter, device is introduced into the venous vasculature superior to heart, advanced to a position adjacent the inter-atrial septum, and used to cut the pVAD drive line adjacent to the inter-atrial septum. After cutting, a first portion of the pVAD is withdrawn from the body via the venous vasculature, and a second portion is withdrawn from the body via the femoral artery.

7 Claims, 6 Drawing Sheets

(56) References Cited

U.S. PATENT DOCUMENTS

| | | | | |
|---|---|---|---|---|
| 2004/0055608 A1* | 3/2004 | Stevens | A61B 90/36 | 128/898 |
| 2005/0192633 A1* | 9/2005 | Montpetit | A61B 17/0469 | 606/232 |
| 2006/0074484 A1* | 4/2006 | Huber | A61B 17/0057 | 623/2.11 |
| 2006/0224110 A1* | 10/2006 | Scott | A61M 1/10 | 604/95.01 |
| 2007/0027456 A1* | 2/2007 | Gartner | A61B 17/0057 | 606/113 |
| 2007/0161845 A1* | 7/2007 | Magovern | A61M 1/3653 | 600/16 |
| 2008/0214888 A1* | 9/2008 | Ben Shalom | A61M 1/122 | 600/17 |
| 2009/0088597 A1* | 4/2009 | Frazier | A61M 1/122 | 600/16 |
| 2009/0149950 A1* | 6/2009 | Wampler | A61M 1/1022 | 623/3.13 |
| 2009/0192579 A1* | 7/2009 | Ransbury | A61M 39/0613 | 607/119 |
| 2010/0004501 A1* | 1/2010 | Whisenant | A61M 27/002 | 600/16 |
| 2010/0076247 A1* | 3/2010 | Zilbershlag | A61M 1/1031 | 600/17 |
| 2011/0118537 A1* | 5/2011 | Wampler | A61M 1/12 | 600/17 |
| 2011/0130619 A1* | 6/2011 | Whisenant | A61M 1/12 | 600/16 |
| 2011/0190683 A1* | 8/2011 | Gellman | A61M 25/0023 | 604/6.16 |
| 2011/0201990 A1* | 8/2011 | Franano | A61M 1/367 | 604/9 |
| 2012/0296358 A1* | 11/2012 | Nguyen | A61B 17/11 | 606/170 |
| 2013/0066342 A1* | 3/2013 | Dell | A61B 17/10 | 606/151 |
| 2015/0230811 A1* | 8/2015 | Kovarik | A61B 1/24 | 433/29 |
| 2018/0099078 A1* | 4/2018 | Tuseth | A61M 1/1008 | |
| 2019/0125948 A1* | 5/2019 | Stanfield | A61M 1/122 | |
| 2019/0201015 A1* | 7/2019 | Kovarik | A61B 1/0684 | |
| 2019/0209758 A1* | 7/2019 | Tuval | A61B 5/0215 | |
| 2019/0239890 A1* | 8/2019 | Stokes | A61B 34/25 | |

* cited by examiner

DEVICES FOR USE IN EXTRACTING PERCUTANEOUS VENTRICULAR ASSIST DEVICES

BACKGROUND

Percutaneous ventricular assist devices (pVADs) are pump devices positioned within the heart and used for circulatory support. In order for these pVADs to be considered minimally invasive, interventional cardiology-based procedures, they must enter the heart from a percutaneous puncture of a peripheral vessel. If the devices are thin and flexible, they may be introduced in an artery and advanced retrograde across the aortic valve to the left ventricle. If they are too large to enter an artery, they may be introduced into larger peripheral veins but then they must cross from the right side of the heart to the left side across the inter-atrial septum in a well-established but tortuous route via a technique known as transseptal catheterization. However, because of the combined large size and/or rigidity of these high cardiac output pVADS, generally the transseptal route has proven to be extremely difficult. The traditional transseptal approach involves driving a therapeutic device over a 0.035 in. guidewire that has been previously introduced across the interatrial septum, through the left atrium then across the mitral valve and into the left ventricle. This guidewire provides a flexible track over which these large devices can potentially be forced into position. However, high cardiac output pVADs are too big and too rigid to easily negotiate the tight bends that are required when crossing into and navigating through the left atrium. As a result, they can fail to follow the course of the guidewire and continue in a relatively straight course when attempting to negotiate the multiple turns required, causing both the deformed guidewire and tip of the therapeutic device to protrude into the delicate cardiac tissues.

U.S. application Ser. No. 16/578,375, filed 22 Sep. 2019, entitled Systems and Methods for Transseptal Delivery of Percutaneous Ventricular Assist Devices and Other Non-Guidewire Based Transvascular Therapeutic Devices, and incorporated herein by reference discloses a system and method for delivering cardiac therapeutic devices positionable at the aortic valve, including pVADs, to the heart, together with exemplary methods for using those systems using superior access.

Under certain circumstances it might become necessary to remove a pVAD after it has been positioned. This application describes instruments that may be used for pVAD extraction should it become necessary.

DETAILED DESCRIPTION

This application describes instrument that may be used to cut a pVAD device that has been implanted within a patient so that it may be withdrawn from the patient.

Figure 1:
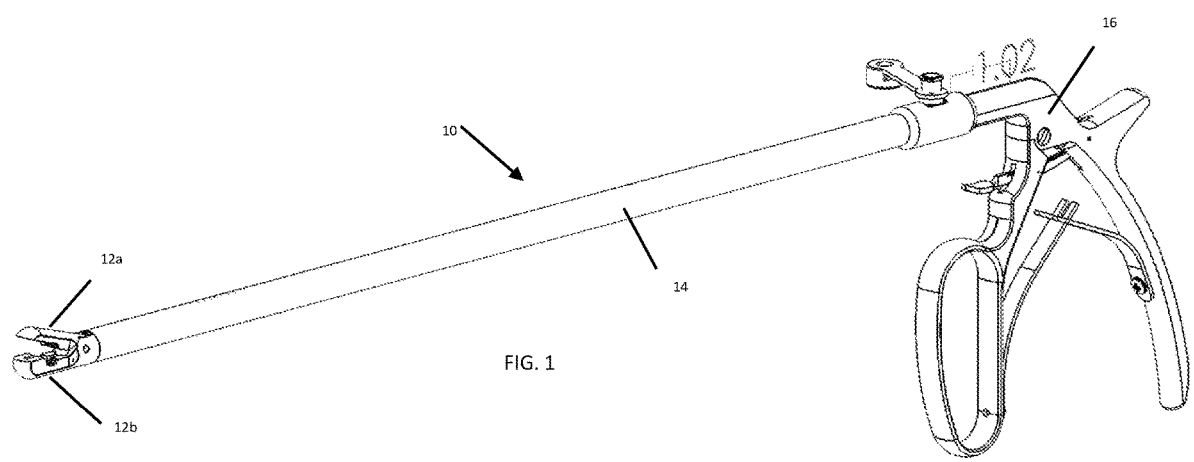
FIG. 1 is a perspective view of a first embodiment of a device suitable for use in extracting a percutaneous ventricular assist device.
Figure 2A:
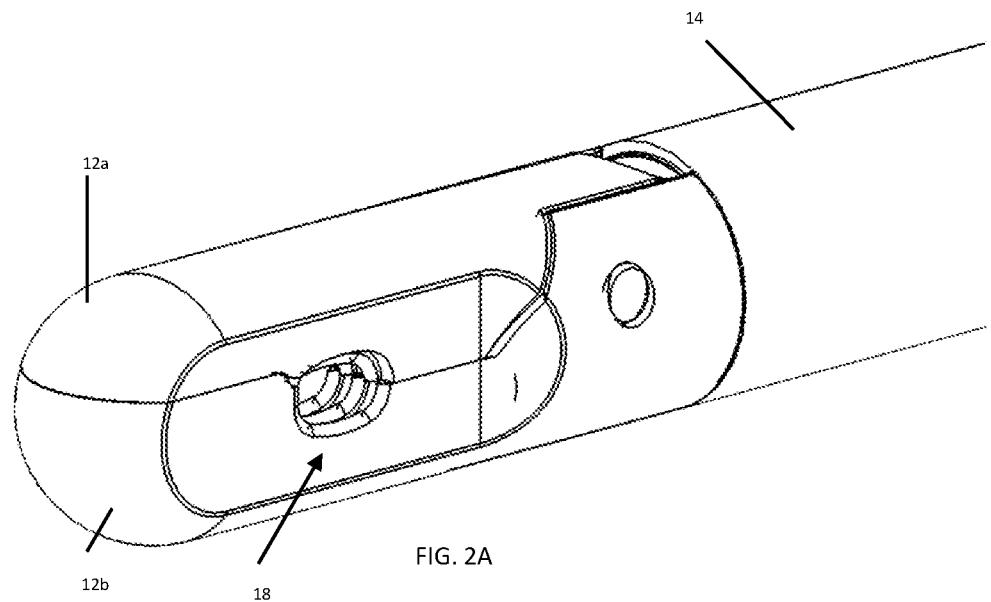
FIG. 2A is a perspective view of the distal end of the device of FIG. 1 with the jaws in the closed position.

A first embodiment of an instrument 10 is shown in FIG. 1. Instrument 10 includes a distal end having jaws, 12a, 12b one or both of which are moveable to transition the jaw between the closed position shown in FIG. 2A and the open position shown in FIG. 2B. In the embodiment that is shown, jaw 12b is a fixed jaw and jaw 12a is pivotable to open and close the jaws.

The jaws 12a, 12b are positioned on the distal end of a flexible shaft 14. The shaft is of sufficient length to extend from the right internal jugular vein into the right atrium and to the inter-atrial septum. At the proximal end of the shaft 14 is a handle 16 including actuators operable to move the jaws between the open and closed position, and to drive a cutting blade (described below) that runs longitudinally between the jaws.

The jaws are shaped to together define a laterally-extending passage 18 when in the closed position. See FIG. 2A. During use this passage is closed around a portion of the pVAD drive line that is to be cut and extracted.

Figure 2B:
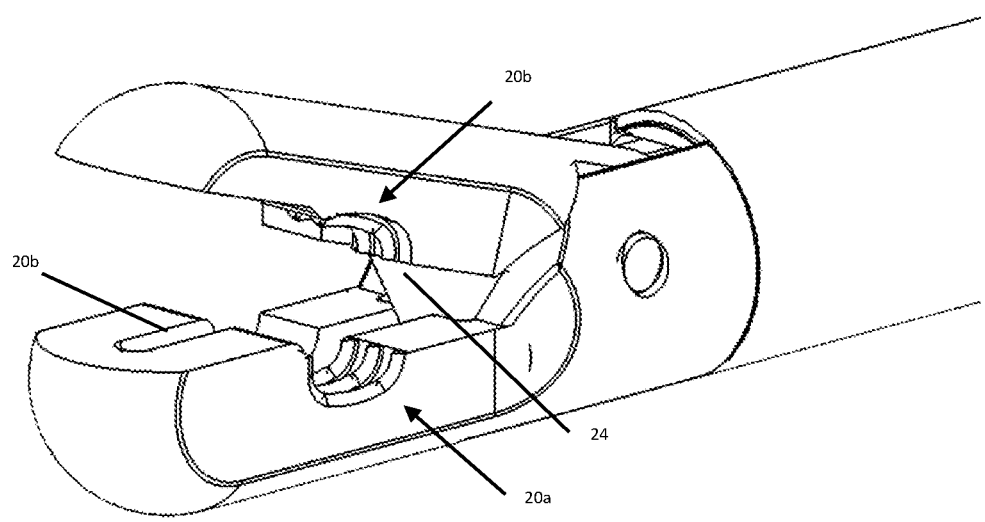
FIG. 2B is a perspective view of the distal end of the device of FIG. 1 with the jaws in the open position.

Ribs 20a, 20b on the jaws 12a, 12b line the passage 18 as shown in FIG. 2B. The ribs preferably extend in a longitudinal direction and together form an enclosed gripping area within the passage, allowing the jaw members 12a, 12b to maintain a secure grip, on at least one side of the blade channel, on the portion of the pVAD drive line extending through the lumen.

Figure 3A:
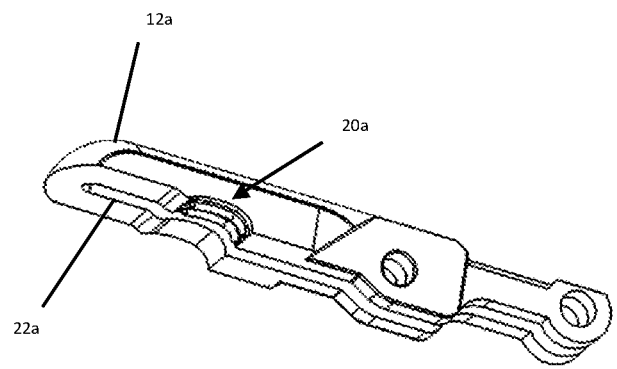
FIG. 3A is a perspective view of the upper jaw member of the cutting and grasping device of FIG. 1.
Figure 3B:
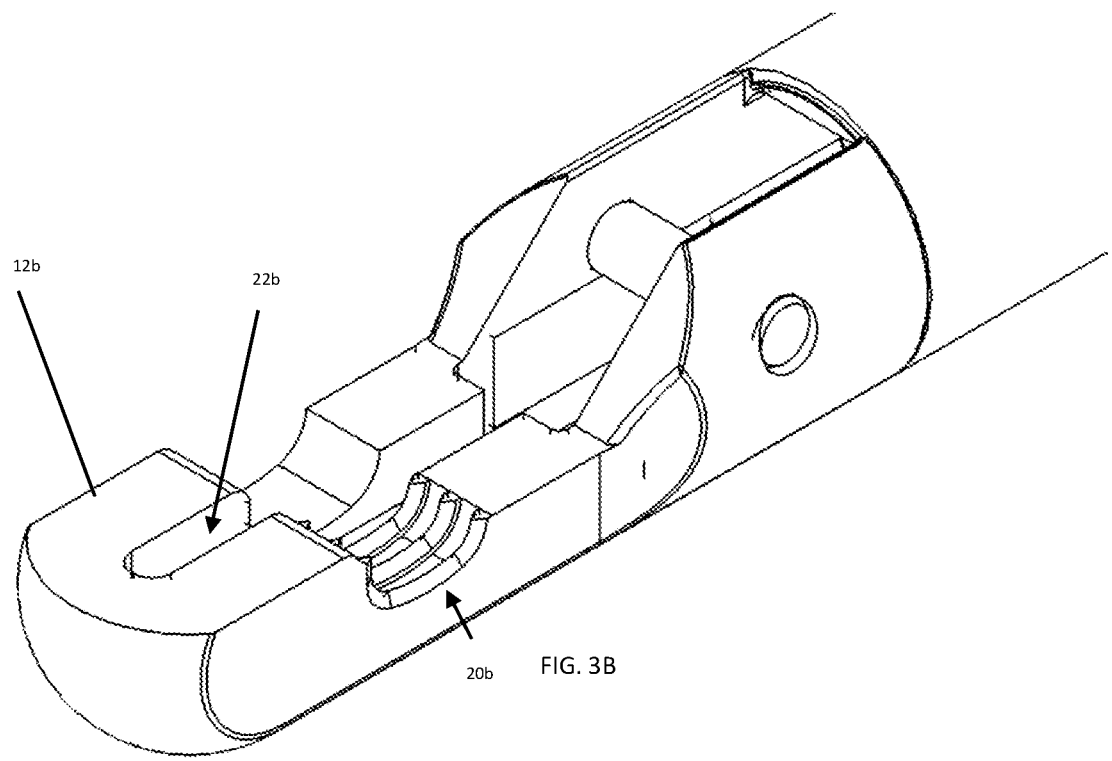
FIG. 3B is a perspective view of the lower jaw member of the cutting and grasping device of FIG. 1. For clarity the blade is not shown in FIG. 3B.

Longitudinally extending channels 22a, 22b, best seen in FIGS. 3A and 3B, are positioned to define a blade channel when the jaws are closed. The blade 24 (FIG. 2B) is advanceable through the blade channel to cut the portion of the pVAD situated in the laterally-extending lumen.

Figure 4:
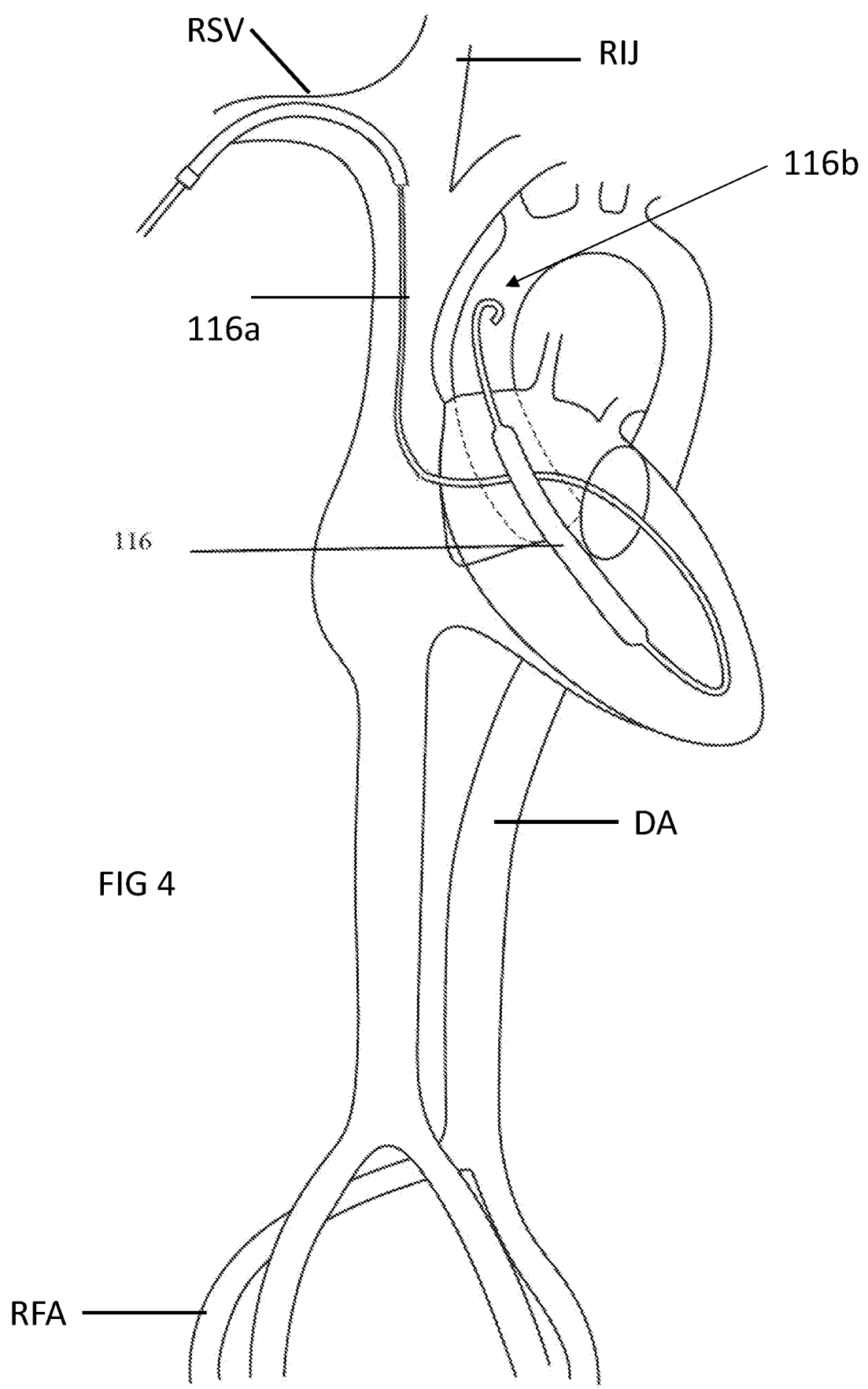
FIG. 4 schematically illustrates a pVAD implanted in the heart prior to extraction.
Figure 6:
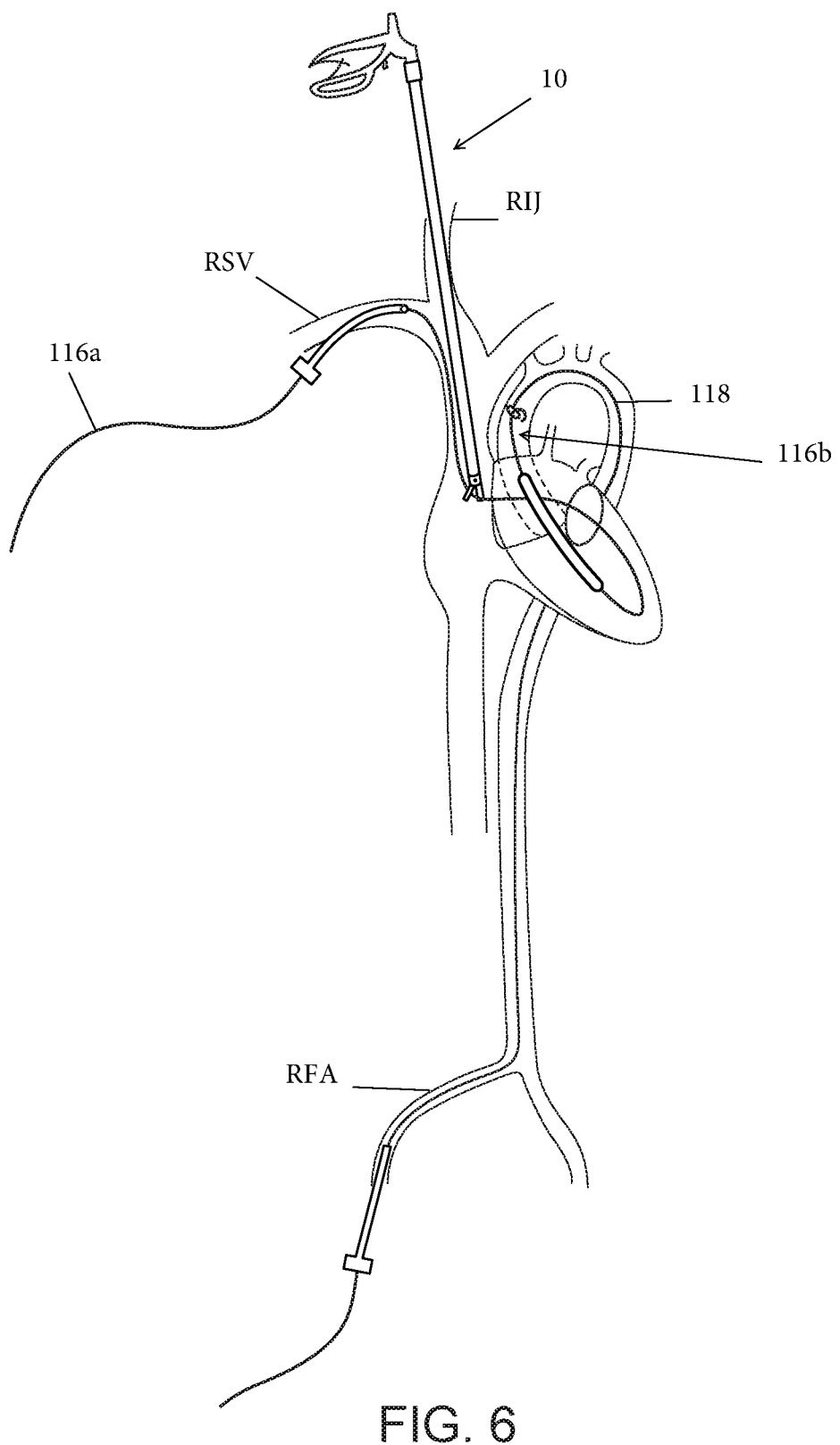
FIG. 6 schematically illustrates use of an extraction device in a method for extracting a pVAD.

Use of the device 10 will next be described in the context of a pVAD device 116 that has been positioned as shown in FIG. 4 and in accordance with the applications discussed in the Background. The drive line 116a of the pVAD extends out the right atrium to the vena cava to the right subclavian vein (RSV) and out of the body via an RSV sheath. The pump crosses the aortic valve and has an attached pigtail connector 116b in the aorta. Should it become necessary to remove the pVAD, a snare catheter 118 is advanced from the right femoral artery (RFA) through the descending aorta DA and used to capture the pigtail 116b of the pVAD within the aorta, as shown in FIG. 6. This ensures the distal part of the pVAD is secured when the drive line is cut.

The cutting device 10 is inserted into a sheath previously inserted into the right internal jugular vein (RH), and its jaws 10 are advanced to and into the right atrium. It is positioned with the jaw members 12a, 12b adjacent to the right side of the inter-atrial septum. The jaw members 12a, 12b are closed over the drive line, oriented with the ribs 20a, 20b closed on the portion of the drive line that is closest to the interatrial septum. Then the blade is advanced through the jaws, severing the pVAD drive line at the inter-atrial septum. To facilitate cutting, slight tension may be applied to the drive line by pulling the drive line from the RSV. When the practitioner is ready to withdraw the venous side of the drive line, the jaws are opened slightly to release the cut ends from the ribs of the jaws. The venous side of the drive line is then withdrawn through the original right subclavian sheath through which the drive line 116*a* extends. The cutting device 10 is withdrawn from the internal jugular sheath and the pVAD is withdrawn from the right femoral artery using the snare 118.

Figure 5A:
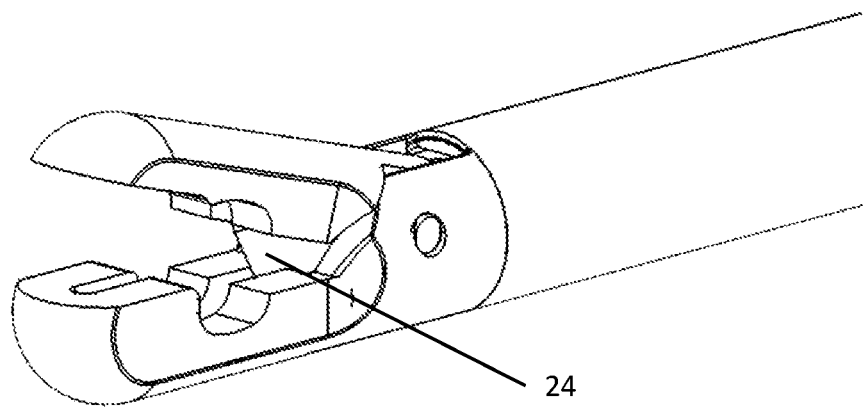
FIG. 5A is a perspective view of the distal end of a second embodiment, with the jaws in the open position.
Figure 5B:
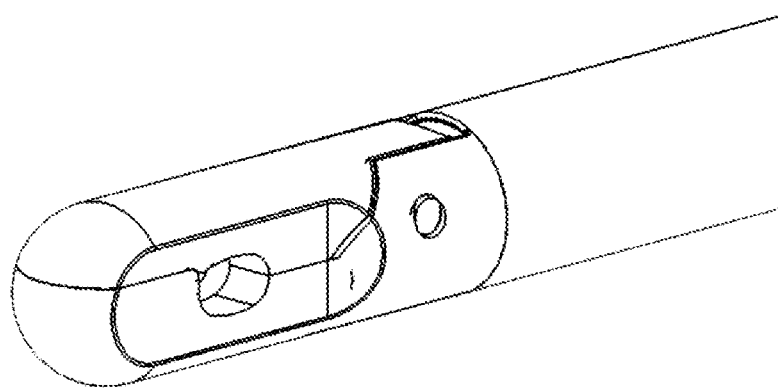
FIG. 5B is a perspective view of the distal end of the second embodiment, with the jaws in the closed position.

A second embodiment shown in FIGS. 5A, 5B, this embodiment is similar to the first embodiment, but is provided without the ribs.

What is claimed is:

1. A method of extracting a pVAD device implanted in a heart of patient, the pVAD positioned with a distal portion in an aorta of the heart and a drive line extending across an inter-atrial septum and out of the body via a superior vessel of the venous vasculature, the method comprising:
    engaging a distal part of the pVAD device in the aorta of a patient using an engaging instrument introduced into a femoral artery and through the descending aorta;
    introducing a cutter into the venous vasculature superior to heart and advancing the cutter to a position adjacent to an inter-atrial septum;
    cutting the pVAD drive line adjacent to the inter-atrial septum using the cutter, while the distal part of the pVAD device is engaged in the aorta by the engaging instrument;
    withdrawing a first portion of the pVAD from the body via the venous vasculature; and
    withdrawing a second portion of the pVAD from the body via the femoral artery.

2. The method of claim 1, wherein the step of introducing the cutter introduces the cutter via the right internal jugular vein.

3. The method of claim 2, wherein the step of withdrawing the first portion withdraws the first portion through a right subclavian vein.

4. The method of claim 3, wherein prior to extraction, the pVAD is positioned with the drive line extending out of the body via the right subclavian vein.

5. The method of claim 1, wherein cutting the pVAD drive line includes clamping the drive line between jaws of the cutter, and then longitudinally advancing a cutting blade through the closed jaws to sever the drive line.

6. The method of claim 5, wherein the cutter is provided to have jaws that define a passage when in a closed position, wherein clamping the drive line includes moving the jaws to the closed position, and wherein longitudinally advancing the blade includes advancing the cutting blade longitudinally relative to the jaws through the passage.

7. The method of claim 1, wherein the method is for extracting a pVAD having a distal pigtail connector positioned with a distal portion in an aorta of the heart and a drive line extending through a left ventricle and mitral valve, across an inter-atrial septum and out of the body via a superior vessel of the venous vasculature, and wherein:
    the engaging step engages the pigtail connector of the pVAD within the aorta.

* * * * *